(12) United States Patent
Harima

(10) Patent No.: US 7,134,602 B2
(45) Date of Patent: Nov. 14, 2006

(54) HEALTH CARE APPARATUS

(75) Inventor: Shinichi Harima, Fujimi (JP)

(73) Assignee: Tanita Corporation, Tokyo (JP)

( * ) Notice: Subject to any disclaimer, the term of this patent is extended or adjusted under 35 U.S.C. 154(b) by 264 days.

(21) Appl. No.: 10/854,234

(22) Filed: May 27, 2004

(65) Prior Publication Data

US 2004/0238641 A1     Dec. 2, 2004

(30) Foreign Application Priority Data

May 28, 2003    (JP)   ............... 2003-151281

(51) Int. Cl.
*G06K 7/10*     (2006.01)
(52) U.S. Cl. ............ 235/472.01; 235/472.02; 235/472.03
(58) Field of Classification Search ........... 235/472.01, 235/472.02, 472.03, 462.45
See application file for complete search history.

(56) References Cited

U.S. PATENT DOCUMENTS

| 4,703,756 A | 11/1987 | Gough et al. |
| 6,096,275 A | 8/2000 | Greenberg |
| 2001/0047252 A1 | 11/2001 | Brown |
| 2003/0004403 A1 | 1/2003 | Drinan et al. |
| 2003/0065561 A1 | 4/2003 | Brown et al. |
| 2004/0248204 A1* | 12/2004 | Moerman .................. 435/7.1 |

FOREIGN PATENT DOCUMENTS

| EP | 0 878 713 A2 | 11/1998 |
| JP | 9-327443 | 12/1997 |
| JP | 3117192 | 10/2000 |
| JP | 2002-207037 A | 7/2002 |
| WO | WO 00/78208 A1 | 12/2000 |
| WO | WO 01/39089 A1 | 5/2001 |
| WO | WO 03/015005 A2 | 2/2003 |

* cited by examiner

*Primary Examiner*—Karl D Frech
(74) *Attorney, Agent, or Firm*—McDermott Will & Emery LLP

(57) ABSTRACT

Disclosed is a health care apparatus, comprising: a measurement unit; an input unit; and a health index calculation unit. According to the present invention said measurement unit measures an oxidation/reduction potential of a body of a person, and said input unit enters at least one of living body information other than said oxidation/reduction potential of the body. Furthermore, said health index calculation unit calculates a health index for judging a health condition, based on said oxidation/reduction potential of the body and said living body information.

5 Claims, 9 Drawing Sheets

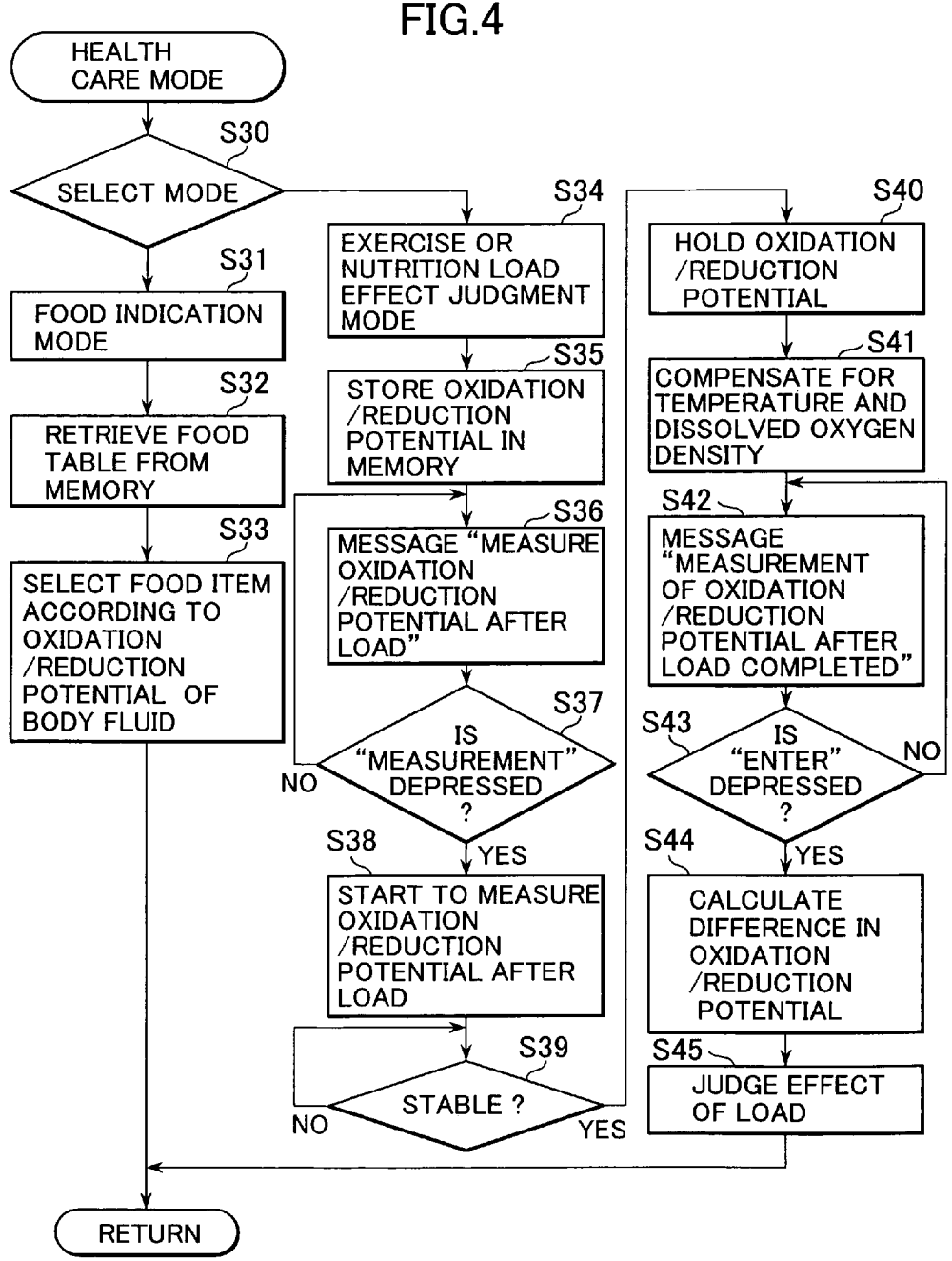

FIG.5

| HEALTH LEVEL | 0 | 1 | 2 | ... | 8 | 9 | 10 |
|---|---|---|---|---|---|---|---|
| OXIDATION/REDUCTION POTENTIAL (mv) | NOT LESS THAN +250 | +250~+200 | +200~+150 | ... | -100~-150 | -150~-200 | NOT GREATER THAN -200 |
| HIGHEST BLOOD PRESSURE (mmHg) | NOT LESS THAN 160 | 160~155 | 155~150 | ... | 125~120 | 120~115 | 110~115 |
| LOWEST BLOOD PRESSURE (mmHg) | NOT GREATER THAN 65 | 65~70 | 70~75 | ... | 100~105 | 105~110 | 75~80 |
| | NOT LESS THAN 107 | 107~104 | 104~101 | ... | 86~83 | 83~80 | |
| | NOT GREATER THAN 48 | 48~51 | 51~54 | ... | 69~72 | 72~75 | |
| BMI – MALE (kg/cm²) | NOT LESS THAN 31 | 31~30 | 30~29 | ... | 24~23 | 23~22 | 21~22 |
| | NOT GREATER THAN 12 | 12~13 | 13~14 | ... | 19~20 | 20~21 | |
| BMI – FEMALE (kg/cm²) | NOT LESS THAN 32 | 32~31 | 31~30 | ... | 25~24 | 24~23 | 22~23 |
| | NOT GREATER THAN 13 | 13~14 | 14~15 | ... | 20~21 | 21~22 | |
| BLOOD SUGAR VALUE AT EMPTY STOMACH (mg/dl) | NOT LESS THAN 120 | 120~115 | 115~110 | ... | 85~80 | 80~75 | 70~75 |
| | NOT GREATER THAN 25 | 25~30 | 30~35 | ... | 60~65 | 65~70 | |
| URIC ACID VALUE – MALE (mg/dl) | NOT LESS THAN 8.5 | 8.5~8.1 | 8.1~7.7 | ... | 5.7~5.3 | 5.3~5.0 | 4.7~5.0 |
| | NOT GREATER THAN 2.0 | 2.0~2.3 | 2.3~2.6 | ... | 4.1~4.4 | 4.4~4.7 | |
| URIC ACID VALUE – FEMALE (mg/dl) | NOT LESS THAN 7.5 | 7.5~7.1 | 7.1~6.7 | ... | 4.7~4.3 | 4.3~4.0 | 3.7~4.0 |
| | NOT GREATER THAN 1.0 | 1.0~1.3 | 1.3~1.6 | ... | 3.1~3.4 | 3.4~3.7 | |
| PULSE RATE AT REST (Pulses/min) | NOT LESS THAN 97 | 97~94 | 94~91 | ... | 76~73 | 73~70 | 65~70 |
| | NOT GREATER THAN 38 | 38~41 | 41~44 | ... | 59~62 | 62~65 | |
| URINE SUGAR VALUE (mg/dl) | NOT LESS THAN 500 | 400~500 | 300~400 | ... | 50~100 | 0~50 | 0 |
| RATIO OF Na/K IONS | NOT LESS THAN 11 | 10~11 | 9~10 | ... | 3~4 | 2 | 1 |

FIG.7

FOOD TABLE

| OXIDATION/REDUCTION POTENTIAL OF BODY FLUID | FOOD ITEMS THAT MAY BE INGESTED |
|---|---|
| 0～+20 | CARROT, RADISH, LIVER |
| −20～0 | SPINACH, TOMATO |
| −40～−20 | SOYBEAN, BURDOCK |
| −60～−40 | STRAWBERRY, SPORTS DRINK |
| −80～−60 | LEMON, ORANGE |
| −100～−80 | PORK, CHICKEN |

HEALTH CARE APPARATUS

BACKGROUND OF THE INVENTION

1. Field of the Invention

The present invention relates to a health care apparatus for judging health condition of a person by measuring an oxidation/reduction potential of the person's body.

2. Prior Art

A health care apparatus has been disclosed in the art in which an oxidation/reduction potential of body fluid such as saliva, urine, sweat, blood, etc. is measured and it is used as the parameter for judging the body condition or health level of a person (refer to e.g. Patent Document 1).

Another health care apparatus has also been disclosed in which an oxidation/reduction potential is classified into a plurality of levels and some concrete names of diseases are assigned at each of the levels (refer to Patent Document 2).

Patent documents associated with the present invention are as follows:

Patent Document 1: Japanese Patent No. 3117192

Patent Document 2: Japanese Patent Laid-Open No. 2002/207037

However, the prior art health care apparatus are configured to indicate the body condition, health level, and degree of progress of a disease by only using the oxidation/reduction potential as the judgment criterion, but not taking into account of living body information and food ingestion information for a person under test. Accordingly, the prior art apparatus provide so-called a gray zoon within which both a normal person and a person who suffers from some disease are present if they have the oxidation/reduction potential ranging from +10 to +50 (mV), for example. In particular, suspected persons having no self-knowledge, but latently having some disease are included in the gray zoon. That is to say, the judgment criterion using only the oxidation/reduction potential is ambiguous in distinguishing the normal person from the person who suffers from some disease.

In addition, measurement of the oxidation/reduction potential greatly depends on the measurement condition such as temperature of an object to be measured and presence of dissolved oxygen. In particular, it is apparent that measurement of the oxidation/reduction potential of the living body, carried out with small volume of body fluid, for example, may lead to greater error.

In view of the above it is an object of the present invention to solve the problems of the prior art, as described above, and to provide a new and improved health care apparatus for providing highly precise and useful living body information on the basis of an oxidation/reduction potential of body fluid of a person under test and other data information, and more particularly, to provide a health care apparatus for indicating health condition of a person under test with higher precision by taking into account of living body information, in addition to an oxidation/reduction potential of body fluid of the person or alternatively a health care apparatus for providing highly precise and useful living body control information by taking into account of time series data and clock data, in addition to an oxidation/reduction potential of body fluid of the person.

SUMMARY OF THE INVENTION

In order to attain such object the present invention provides a health care apparatus, comprising: a measurement unit; an input unit; and a health index calculation unit, wherein said measurement unit measures an oxidation/reduction potential of a body of a person, said input unit enters at least one of living body information other than said oxidation/reduction potential of the body, and said health index calculation unit calculates a health index for judging a health condition, based on said oxidation/reduction potential of the body and said living body information.

According to an embodiment of the present invention the health care apparatus further comprises a health age judgment unit, said health age judgment unit judges an age for health, based on said health index and according to a regression formula derived from correlation between said health index and the age.

According to another embodiment of the present invention said input means enters at least one of blood pressure value, uric acid value, blood sugar value, ratio of sodium/potassium ions, pulse rate, and BMI as said living body information other than said oxidation/reduction potential of the body.

According to further embodiment of the present invention said health index calculation unit calculates the health index according to a health level that is determined by comparing said oxidation/reduction potential of the body and said living body information with an associated health level assessment criterion in which a plurality of health levels is set in advance.

According to yet further embodiment of the present invention the health care apparatus further comprises: a difference calculation unit; a load effect calculation unit; and a load-to-health index calculation unit, wherein said difference calculation unit calculates any difference in oxidation/reduction potential before and after application of load to the body, said load including an action of doing an exercise, taking a meal, etc., said load effect calculation unit calculates any effect of load on the body by comparing said difference in oxidation/reduction potential before and after application of load with a load effect assessment criterion in which a plurality of load effect levels is set in advance, and said load-to-health index calculation unit calculates a load-to-health index for judging a health condition due to application of load to the body, based on said effect of load and said living body information.

According to yet further embodiment of the present invention said living body information is at least one of blood pressure value, uric acid value, blood sugar value, urine sugar value, pulse rate, and ratio of sodium/potassium ions (hereafter referred to as "ratio of Na/K ions").

According to yet further embodiment of the present invention said living body information is data of adiposity such as body weight, BMI (Body Mass Index) or body fat.

In another aspect the present invention provides a health care apparatus, comprising: a measurement unit; a clock unit; a memory unit; and a living body change acquierement unit, wherein said measurement unit measures an oxidation/reduction potential of a body of a person, said clock unit determines date and time at which the measurement is done, said memory unit stores said oxidation/reduction potential of the body and said date and time as the time series data, and said living body change acquirement unit acquires any time series living body change such as a menstrual cycle, restoration after disease, etc., from said time series data.

According to an embodiment of the present invention the health care apparatus further comprises a food indication unit, said food indication unit indicates at least one of the following food items: one is exhibiting the same oxidation/reduction potential as that of the person's body; and the other is exhibiting an oxidation/reduction potential desired for intake in view of the oxidation/reduction potential of the person's body, those food items being selected from among a food table listing several food items classified into a plurality of groups in advance according to the oxidation/reduction potential values that they inherently have.

According to another embodiment of the present invention the health care apparatus further comprises a dissolved oxygen density compensation unit, said compensation unit compensates for any effect of density of dissolved oxygen when measuring the oxidation/reduction potential of the body.

According to further embodiment of the present invention the health care apparatus further comprises a temperature compensation unit, said compensation unit compensates for any effect of temperature of an object to be measured when measuring the oxidation/reduction potential of the body.

BRIEF DESCRIPTION OF THE DRAWINGS

The present invention will be described in more detail with reference to the accompanying drawings, in which:

FIG. 4 is a flow chart illustrating a sub routine for an operation of the health care apparatus;

FIG. 5 shows a health level assessment criterion for determining each health level for each of oxidation/reduction potential value and living body information for a person under test;

FIG. 7 is a food table listing oxidation/reduction potential values and the corresponding foods desired for ingestion;

DESCRIPTION OF THE PREFERRED EMBODIMENTS

Figure 1:
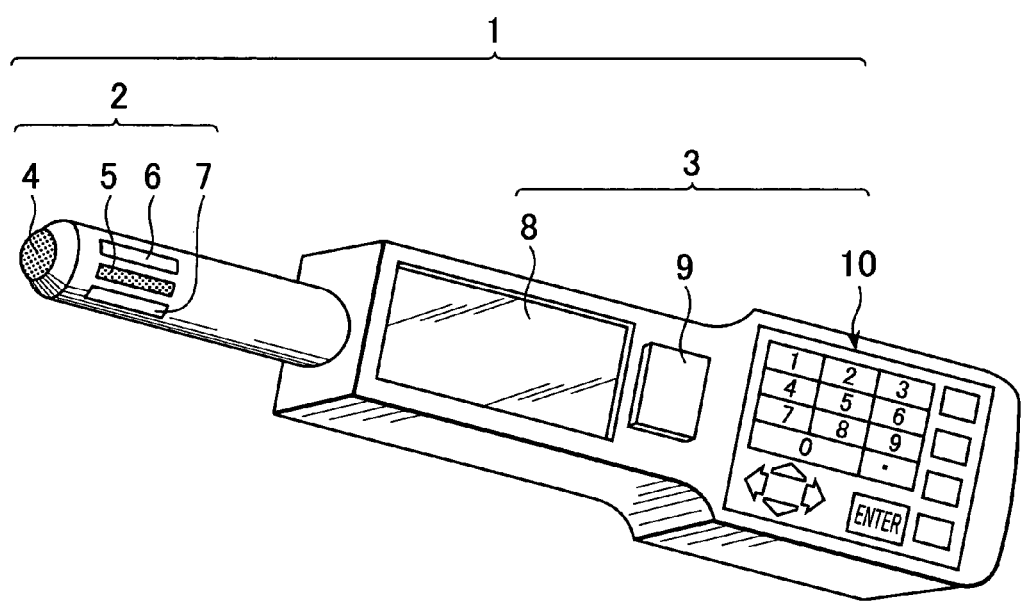
FIG. 1 is an external view of a health care apparatus according to one embodiment of the present invention.

A health care apparatus according to the present invention comprises: a measurement unit; an input unit; and a health index calculation unit, wherein said measurement unit measures an oxidation/reduction potential of a body of a person, said input unit enters at least one of living body information other than said oxidation/reduction potential of the body, and said health index calculation unit calculates a health index for judging a health condition, based on said oxidation/reduction potential of the body and said living body information. Accordingly, the health care apparatus can judge health condition of the person with higher precision by taking into account of the living body information for the person so that a normal person can clearly be distinguished from a person who suffers from a disease.

The health care apparatus further comprises a health age judgment unit which judges an age for health, based on the health index and according to a regression formula derived from correlation between the health index and the age.

In the health care apparatus, the input means enters at least one of blood pressure value, uric acid value, blood sugar value, ratio of sodium/potassium ions, pulse rate, and BMI as said living body information other than the oxidation/reduction potential of the body.

The health index calculation unit calculates the health index according to a health level that is determined by comparing said oxidation/reduction potential of the body and said living body information with an associated health level assessment criterion in which a plurality of health levels is set in advance. Accordingly, any suspected persons latently having any disease can easily be selected from among the normal persons, and the degree of progress of disease that the person suffers from can be indicated.

The health care apparatus further comprises: a difference calculation unit; a load effect calculation unit; and a load-to-health index calculation unit, wherein said difference calculation unit calculates any difference in oxidation/reduction potential before and after application of load to the body, said load including an action of doing an exercise, taking a meal, etc., said load effect calculation unit calculates any effect of load on the body by comparing said difference in oxidation/reduction potential before and after application of load with a load effect assessment criterion in which a plurality of load effect levels is set in advance, and said load-to-health index calculation unit calculates a load-to-health index for judging a health condition due to application of load to the body, based on said effect of load and said living body information. Accordingly, the person can know whether the load of doing an exercise or taking a meal is suitable for him or not.

In one embodiment said living body information is blood pressure value. If the blood pressure increases due to presence of stress an oxidation of body fluid is produced due to active oxygen and lactic acid provided by the stress so that the oxidation/reduction potential of the body is increased. In other words, there is tendency of correlation between the blood pressure value and the oxidation/reduction potential value. Thus, it is possible to know the health condition of a person, taking into account of the presence of stress.

In another embodiment said living body information is uric acid value. The oxidation/reduction potential is changed with the increase/decrease in uric acid which exhibits acidity. Therefore, there is tendency of correlation between the uric acid value and the oxidation/reduction potential value. Thus, it is possible to know the health condition of a person, taking into account of the morbidity and the degree of progress of disease such as gout, hyperlipemia, etc. of which condition is indicated by uric acid value.

In further embodiment said living body information is blood sugar value or urine sugar value. If a person has insufficient insulin due to diabetes or excessive diet, for example, no sugar is dissolved so that the blood sugar value or urine sugar value becomes increased. As the result, fat is consumed as the energy source to form a ketone body that exhibits acidity within the body and to increase the oxidation/reduction potential value. Therefore, there is tendency of correlation between the blood sugar value or urine sugar value and the oxidation/reduction potential value. Thus, it is possible to know the health condition of a person, taking into account of the danger of diabetes or excessive diet that may lead to insufficient insulin.

In yet further embodiment said living body information is the ratio of Na/K ions. This is provided by measuring both ion densities of sodium (hereafter referred to as "Na") and potassium (hereafter referred to as "K") in the body fluid such as saliva, urine, sweat, blood, etc., using Polarograph type ingredient meter, for example. It is well known that excessive intake of "Na" is one of the factors for higher blood pressure and intake of "K" expels "Na" outside the body to lower the blood pressure. In other words, if "Na" ion density in extracellular fluid becomes higher the extracellular fluid is increased to keep the "Na" ion density constant. As the result, the blood pressure is increased to keep the flow rate of the blood. Because of correlation between blood pressure value and the oxidation/reduction potential value, as described above, it can also be said that there is tendency of correlation between the ratio of Na/K ions and the oxidation/reduction potential value. Thus, it is possible to know the health condition of a person, taking into account of blood pressure.

In yet further embodiment of the present invention said living body information is data of adiposity such as body weight, BMI or body fat, which has been utilized as the well known index for indicating the morbidity for adult noncommunicable diseases such as diabetes, hyperlipemia, etc. Such adult noncommunicable diseases may be indicated by blood pressure, uric acid value, or blood sugar value, which living body information has tendency of correlation with the oxidation/reduction potential value, as described above. Therefore, there is tendency of correlation between the data of adiposity and the oxidation/reduction potential value. Thus, it is possible to know the health condition of a person, taking into account of the morbidity for adult noncommunicable diseases.

In yet further embodiment of the present invention said living body information is pulse rate which has tendency of increase if heart and lung function becomes lower with the progress of adiposity. Therefore, there is tendency of correlation between the pulse rate and the data of adiposity such as body weight, BMI or body fat. Because of correlation between the data of adiposity such as body weight, BMI or body fat and the oxidation/reduction potential value, as described above, there is tendency of correlation between the pulse rate and the oxidation/reduction potential value. Thus, it is possible to know the health condition of a person, taking into account of the condition of heart and lung function.

Furthermore, the health care apparatus according to the present invention comprises: a measurement unit; a clock unit; a memory unit; and a living body change acquirement unit, wherein said measurement unit measures an oxidation/reduction potential of a body of a person, said clock unit determines date and time at which the measurement is done, said memory unit stores said oxidation/reduction potential of the body and said date and time as the time series data, and said living body change acquirement unit acquires any time series living body change such as a menstrual cycle, restoration after disease, etc., from said time series data. Accordingly, healthcare for a normal person or a person who suffers from a disease can easily be performed for longer period of time.

The health care apparatus further comprises a food indication unit, said food indication unit indicates at least one of the following food items: one is exhibiting the same oxidation/reduction potential as that of the person's body; and the other is exhibiting an oxidation/reduction potential desired for intake in view of the oxidation/reduction potential of the person's body, those food items being selected from among a food table listing several food items classified into a plurality of groups in advance according to the oxidation/reduction potential values that they inherently have. Accordingly, which food item having the same oxidation/reduction potential as that of body fluid of a person under test can be displayed, thereby enabling measurement with pleasure and spontaneously getting the knowledge about how much degree of oxidation/reduction the food items inherently has. On the other hand, by displaying food items each having oxidation/reduction potential desired for intake the person under test can know which food item is suitable for him and can control his body condition due to the food item.

The health care apparatus further comprises a dissolved oxygen density compensation unit, said compensation unit compensates for any effect of density of dissolved oxygen when measuring the oxidation/reduction potential of the body. Accordingly, the degree of oxidation/reduction of the living body can be displayed with higher precision.

The health care apparatus further comprises a temperature compensation unit, said compensation unit compensates for any effect of temperature of an object to be measured when measuring the oxidation/reduction potential of the body. Accordingly, the degree of oxidation/reduction of the living body can be displayed with higher precision.

Now, reference is made to a first embodiment of the present invention which is configured to provide health care for a person under test by indicating each type of health index and each kind of food item suitable for health condition of the person, based on an oxidation/reduction potential of body fluid of the person and other living body information such as blood pressure, uric acid value, blood sugar value, body weight, etc.

A health care apparatus of the present invention will be described hereafter with reference to FIGS. 1 and 2. FIG. 1 is a perspective view of the health care apparatus 1 according to the first embodiment of the present invention. The health care apparatus 1 comprises a sensor section 2 and a body section 3. In particular, the sensor section 2 includes a work electrode 4 for measuring an oxidation/reduction potential of body fluid of a person under test, and a reference electrode 5. The sensor section 2 further includes a temperature sensor 6 for measuring the temperature of an object to be measured and a dissolved oxygen density sensor 7 for measuring the density of oxygen in dissolved state. The body section 3 of the apparatus 1 includes a display unit 8 for displaying measurement result, graph or message, a power switch 9 of the apparatus 1, and an operation panel 10 including a ten-key for entering numerical values for living body information and several types of setting keys and a measurement key.

Measurement is performed in such manner that the electrodes and sensors on the sensor section 2 are made contact with the body fluid of the person, such as saliva, urine, sweat, blood, etc.

Figure 2:
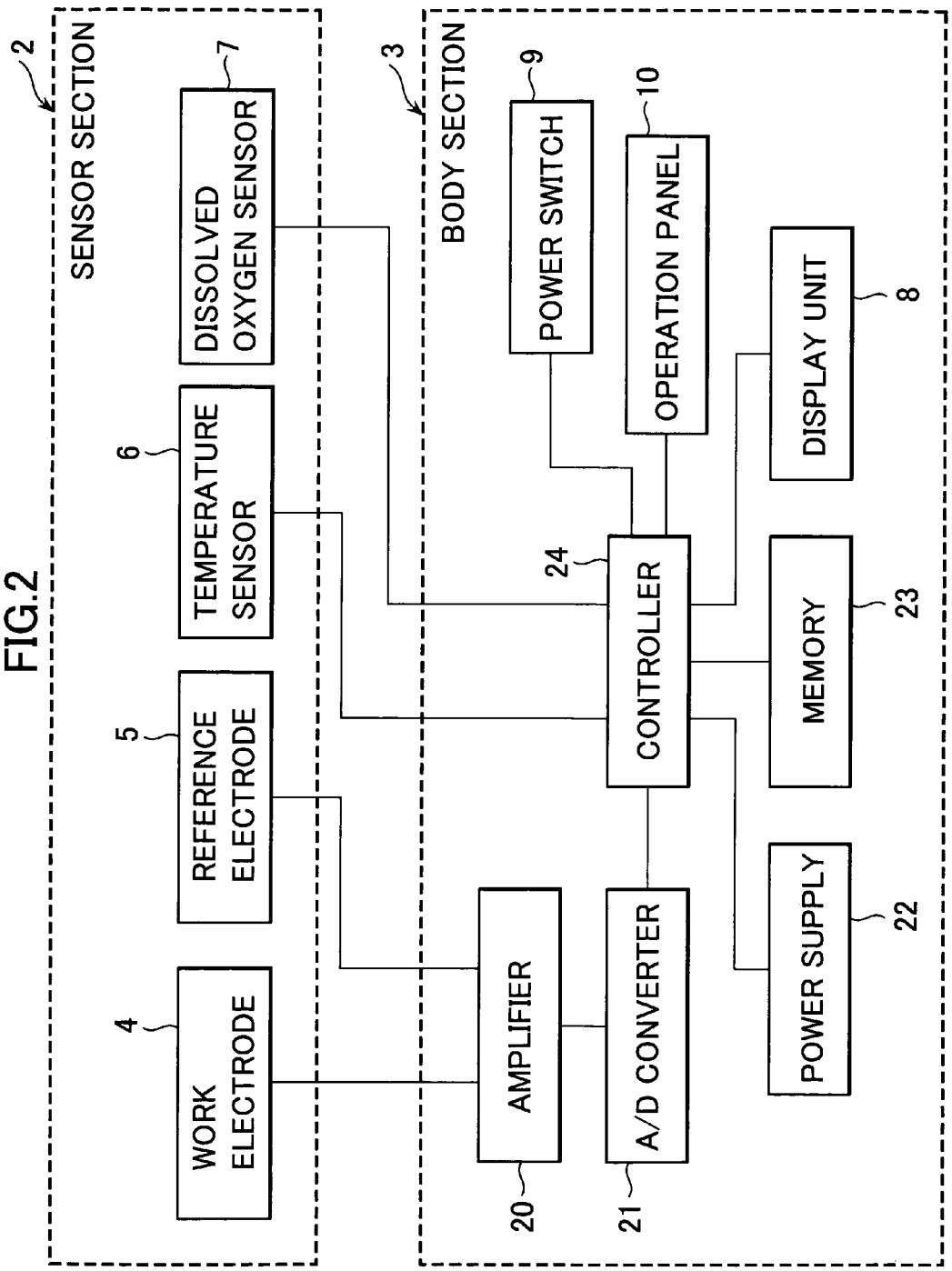
FIG. 2 is a functional block diagram of the health care apparatus.

FIG. 2 is a functional block diagram of the first embodiment. The electrodes and sensors on the sensor section 2 are connected to the body section 3 in the manner as follows: The work electrode 4 and the reference electrode 5 are connected to an amplifier 20 in the body section 3, which amplifies analog signals sent from both electrodes 4, 5. The amplifier 20 is then connected to an A/D converter 21 for converting analog signal into digital signal. The A/D converter 21 is then connected to a controller 24. Also connected to the controller 24 are the temperature sensor 6 and the dissolved oxygen density sensor 7. Furthermore, in the body section 3, the display unit 8 and the operation panel 10 are connected to the controller 24, together with a memory unit 23 for storing the living body information entered from the operation panel 10 and health level assessment criteria described hereafter, and a power supply 22 for providing power to the health care apparatus 1. The controller 24 performs an arithmetic operation and controls operation of the health care apparatus, as described hereafter.

Figure 3:
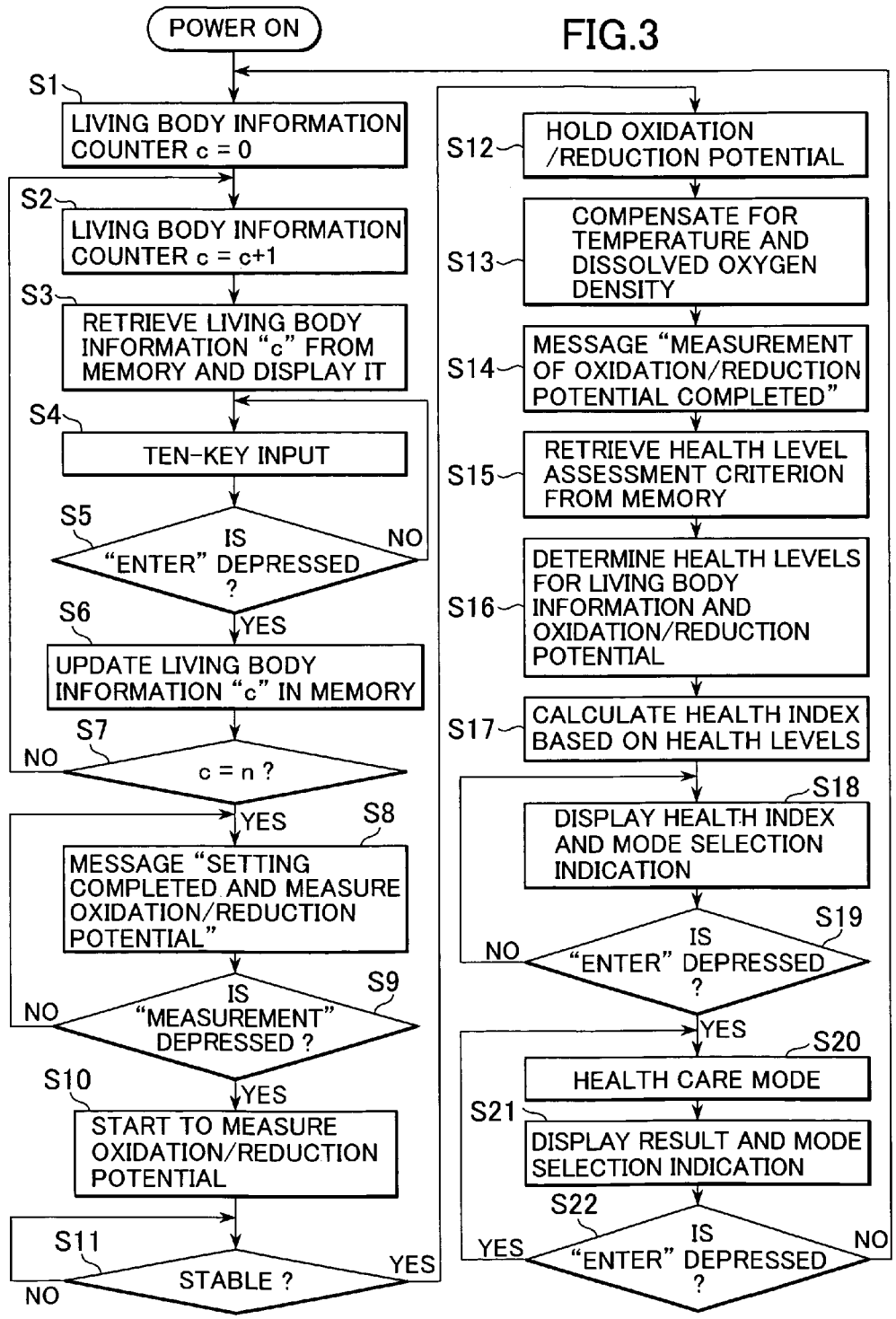
FIG. 3 is a flow chart illustrating a main routine for an operation of the health care apparatus.
Figure 6:
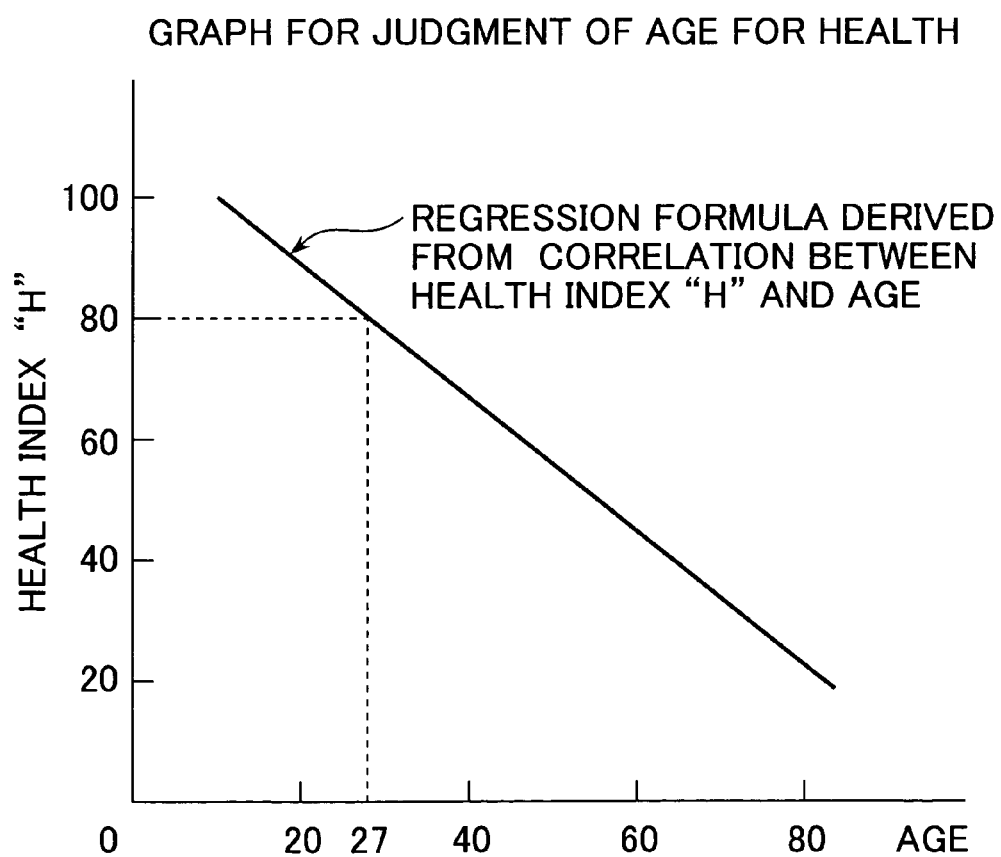
FIG. 6 is a graph for determining an age for health, illustrating a correlation between a health index and the age of the person.

Now, operation of the health care apparatus 1 of the first embodiment will be described with reference to FIGS. 3 to 7. In particular, FIG. 3 shows a main routine for operation of the apparatus 1 and FIG. 4 shows a subroutine for each of health care modes. FIG. 5 shows a health level assessment criterion for determining each health level for each of oxidation/reduction potential values and other living body information for a person under test. FIG. 6 shows a correlation between a health index for a person under test resulting from total combination of the health levels and the age of the person. FIG. 7 is a food table listing the oxidation/reduction potential values and the corresponding food items desired for ingestion.

Initially, the power switch 9 in FIG. 1 is turned ON to power up the health care apparatus 1. At step S1 a living body information counter that has been preset to enter a plurality ("n") of types of living body information is reset (c=0). In this embodiment "n"=8, or eight types of living body information are involved: highest blood pressure, lowest blood pressure, uric acid value, blood sugar value, urine sugar value, "BMI" value, pulse rate, and rate of Na/K ions. Then, at step S2, the living body information counter is incremented by one (c=c+1) in order to set the numerical value for living body information. At step S3 the living body information indicated by the living body information counter is retrieved from the memory 23 and it is displayed on the display unit 8 for entering a numerical value.

At step S4 the numerical value for the living body information that has already been measured is entered via the operation panel 10. Then, at step S5, a check is made to determine whether an "Enter" button on the operation panel 10 is depressed or not. If not, it is interpreted that the numerical value has not been set, and therefore, the routine proceeds via "NO" branch to step S4 where the numerical value is again entered using the ten-key. On the other hand, if "Enter" button is depressed, the routine proceeds to "YES" branch to complete setting the numerical value for the living body information displayed.

Once the living body information has been set in such manner then at step S6 the numerical value for the living body information in the memory 23 is updated. At step S7 a check is made to determine whether the living body information counter reaches the maximum number "n" (c=n). If not, the routine proceeds via "NO" branch to step S2 where the living body information counter is again incremented by one (c=c+1) in order to set the numerical value for other living body information. However, if "c=n" is reached then it is interpreted that setting of all the living body information has been done. Then, the routine proceeds via "YES" branch to step S8 where a message is displayed on the display unit 8 for informing that setting of living body information has been done and for prompting to start measurement of oxidation/reduction potential by depressing a measurement button (not shown) on the operation panel 10.

At step S9 a check is made to determine whether the measurement button is depressed or not. If not, the routine proceeds via "NO" branch to step S8 where the message remains displayed, but if so, the routine proceeds via "YES" branch to step S10 where measurement of oxidation/reduction potential is started.

Then, at step S11, a check is made to determine whether the oxidation/reduction potential being measured reaches stable condition or not. In this connection the oxidation/reduction potential is considered stable if any variation of the oxidation/reduction potential is maintained within the predetermined fixed allowable amplitude range for greater than the fixed time period. If not yet stable, the routine loops via "NO" branch to continue measurement. However, if stable, the routine proceeds via "YES" branch to step S12 where the oxidation/reduction potential is held at that stable condition to provide the stable oxidation/reduction potential value.

Then, at step S13, the stable oxidation/reduction potential value is subjected to compensation for any error due to the temperature of an object to be measured and the density of dissolved oxygen using some well known means. Because of the oxidation/reduction potential susceptible to any environmental condition for measurement the temperature of the object to be measured and the density of dissolved oxygen are measured by the temperature sensor 6 and the dissolved oxygen density sensor 7 in the sensor section 2, respectively. Then, they are compared to the predetermined reference temperature and dissolved oxygen density to provide the temperature and oxygen density compensated oxidation/reduction potential value. In other words, such compensation for the temperature and oxygen density assures that the oxidation/reduction potential value is always considered as such value that is resulted from measurement under the fixed environmental condition.

Then, at step S14, a message is displayed on the display unit 8 for informing that measurement of the oxidation/reduction potential has been done. Thereafter, at step S15, a health level assessment criterion, one example of which is illustrated in FIG. 5, is retrieved from the memory 23. The health level assessment criterion is prepared in such manner that for oxidation/reduction potential value and other living body information a normal range for health level is assigned "Point 10", but a dangerous range for health level in which possibility of suffering from any disease is higher is assigned "Point 0", and the interval therebetween is equally divided. Then, at step S16, each health level is determined on the basis of this health level assessment criterion for each of the oxidation/reduction potential measured as described above and the living body information entered as described above.

At step S17, based on the health levels determined in such manner, a health index for totally identifying the health condition of the person is calculated. For example, a formula for calculating the health index is as follows:

Health Index "*H*"=(average of health levels for living body information)×(health level for oxidation/reduction potential of body fluid)

As the result, the health condition of a person can be judged as compared to the health index "H"=100 where all the health levels belong to the normal range. Furthermore, by using a regression formula resulting from the correlation between the health index "H" and the age of a person it is possible to determine an age for health based on the health index "H", as can be seen in a "graph for determining an age for health" in FIG. 6. It is apparent in the graph of FIG. 6 that if the health index is "H"=80 then the corresponding age for health is determined to be "27" years old.

In this connection, it can be said that there is higher correlation between the health index "H" and the age. It is well known in the art that there is correlation between said living body information and the age. In addition, there is correlation between the oxidation/reduction potential value and the living body information, as described above. However, this is not so higher correlation. Accordingly, multi-regression analysis for the living body information, oxidation/reduction potential and the age has been performed to provide higher correlation between the health index "H" for totally identifying the health condition and the age.

At step S18 the calculated health index, the age for health and the graph for determining an age for health are displayed, together with a message for prompting to select any one of operation modes in which a health care process is carried out in more precisely. Then, at step S19, a check is made to determine whether an "Enter" button is depressed or not. If not, the routine proceeds via "NO" branch to continue to display, as described above. But, if so, the routine proceeds via "YES" branch to step S20 where a health care mode of operation is carried out, as illustrated in a flow chart of subroutine in FIG. 4.

After completion of health care mode of operation in step S20 then at step S21 the result of health care mode of operation is displayed on the display unit 8, together with a message for prompting to select the operation mode once again. Then, at step S22 a check is made to determine whether an "Enter" button is depressed or not. If so, the routine proceeds via "YES" branch to step S20 where the health care mode of operation is carried out, as shown in FIG. 4. But, if not, the routine proceeds via "NO" branch to step S1 after elapsing a fixed time period where the initial setting is performed.

Now, the health care mode of operation performed in step S20 will be described in more detail with reference to the subroutine of FIG. 4. Initially, at step S30 an operation mode is selected from among health care modes of operation displayed on the display unit 8 through the operation panel 10. In this embodiment two health care modes are provided: one is a food indication mode in which the food item desired for intake is indicated; and another is an exercise or nutrition load effect judgment mode in which the effect of an exercise or nutrition load is judged. Each of the health care modes is described hereafter.

If the food indication mode is selected it is recognized by the controller 24 at step S31. This food indication mode provides indication of food item suitable for health condition for a person under test according to the oxidation/reduction potential of body fluid. Then, at step S32, a food table listing the food items suitable for intake is retrieved from the memory 23. The food table lists the food items that may be ingested according to the oxidation/reduction potential values of body fluid. More particularly, the food is classified into several groups of food items according to the degree of oxidation/reduction already measured. As the oxidation/reduction potential of body fluid increases in negative direction even a food item having the oxidation/reduction potential that approaches a positive value may be ingested.

At step S33 comparison is made between the oxidation/reduction potential of body fluid and the food items in the food table, and then, any of food items suitable for health condition of the person under test is selected and indicated. For example, if the oxidation/reduction potential value of body fluid is −80 (mV) which means higher degree of reduction then even a food item having higher degree of oxidation, such as pork or chicken may be ate.

At the same time, by taking into account of other living body information, selection of optimum food item is realized. For example, if uric acid value belongs to health level range "1" which means that paying attention is necessary then a food item such as soybean or burdock is selected and indicated, rather than meat, because it is more suitable for health condition of the person.

After selection of food item in such manner the subroutine returns to main flow chart in FIG. 3 and the result of health care mode is displayed.

On the other hand, if an exercise or nutrition load effect judgment mode is selected at step S30 then it is recognized by the controller 24 at step S34. The exercise or nutrition load effect judgment mode effects to compare the oxidation/reduction potential values before and after application of load and to know whether an action of doing an exercise or taking a meal, which is applied as the load, is suitable for the person or not, based on any change in potential value. Accordingly, at step S35, the stable oxidation/reduction potential value with temperature and dissolved oxygen density compensated for at step S13 in FIG. 3 is stored in the memory 23 as the oxidation/reduction potential value before application of load. Then, at step S36, a message is displayed on the display unit 8 for prompting to start measurement of oxidation/reduction potential after application of load.

At step S37 a check is made to determine whether the measurement button is depressed or not. If not, the subroutine proceeds to "NO" branch to continue to display the message. But, if so, the subroutine proceeds to "YES" branch to measure the oxidation/reduction potential after application of load, as in the case of measurement of the oxidation/reduction potential before application of load. In particular, at step S38, measurement of the oxidation/reduction potential after application of load is started. Then, at step S39, a check is made to determine whether the measurement value reaches stable condition or not. If not, the subroutine proceeds to "NO" branch to repeatedly detect the measurement value, but if so, it proceeds via "YES" branch to step S40 where the oxidation/reduction potential value is held at that stable condition to provide the stable oxidation/reduction potential value.

Then, at step S41, compensation for temperature and dissolved oxygen density is performed under the same condition as that of measurement of oxidation/reduction potential before application of load. Thereafter, at step S42, a message is displayed for informing that measurement of the oxidation/reduction potential after application of load is completed. Then, at step S43, a check is made to determine whether the enter key is depressed to acknowledge the message. If not, the subroutine proceeds to "NO" branch to continue to display the message, but if so, it proceeds via "YES" branch to step S44 where any difference in oxidation/reduction potential before and after application of load is calculated.

Then, at step S45, an effect of the load on the body of a person is judged depending on this difference. In particular, as the difference is changed toward the negative direction the effect of the load is assessed as good for health condition of the person. Thereafter, the subroutine returns to the main flow in FIG. 3 and the result of judgment is displayed.

In the above embodiment the number "n" of living body information that has been set in steps S2 to S7 in FIG. 3 is 8 (or "n"=8). Namely, eight types of living body information each having correlation with the oxidation/reduction potential of the body has been set. However, "n" is not limited to "8" and any number of living body information may be set.

In case where only one of, not a plurality of, living body information is set the health index calculated in step S17 in the flow chart of FIG. 3 indicates the health condition including an effect of the disease specified by that living body information. For example, if the living body information is blood sugar value then the health index calculated using the health level assessment criterion based on the measured oxidation/reduction potential value and the blood sugar value can show how much one's health has been lost due to diabetes or excessive diet involving insufficient insulin, as indicated by blood sugar value. This is also true for urine sugar value. In the same manner, if the living body information is blood pressure value, the health index can show how much one's health has been lost due to the stress. Furthermore, if the living body information is uric acid value, the health index can show a disease such as gout and hyperlipemia. If the living body information is data of adiposity such as body weight, BMI or body fat it can show any adult noncommunicable disease that adiposity relates to, and if the living body information is pulse rate it can show an effect of heart and lung function on one's health. Finally, if the living body information is the ratio of Na/K ions the health index can show the condition of blood flow including blood pressure.

Upon calculating the health index in step S17 in FIG. 3, if even one of the oxidation/reduction potential value and other living body information has health level "0" then the health index "H" is set to "H"=0 which means that a person is not healthy, which can clearly distinguish a normal person from a person who suffers from some disease.

At step S32 in the flow chart of FIG. 4 the food table lists the food items that may be ingested according to the oxidation/reduction potential values of body fluid, as described above. Alternatively, the food table may list the food items each having the same oxidation/reduction potential level as that of the body fluid of a person, which allows to know what food items have the same oxidation/reduction potential level as that of the body fluid of the person. As the result, it becomes possible to perform the measurement with pleasure and to spontaneously get knowledge about how much degree of oxidation/reduction the food items inherently have.

In the exercise or nutrition load effect judgment mode executed at steps S34 to S45 in the flow chart of FIG. 4 the oxidation/reduction potential values before and after the load of doing an exercise or taking a meal are simply measured and compared to each other, as described above. Alternatively, parameters such as type of exercise, extent of exercise, time interval of exercise, etc., in case of the exercise load, or parameters such as name and volume of food item ingested, kind of nutritive elements, etc., in case of the nutrition load may be entered or set as the degree of load. As the result, the effect of the load can more precisely be measured, and it is possible to know which load applied with what extent is better, which is more useful to reconsider the life style and to prevent any adult noncommunicable disease.

Now, reference is made to a second embodiment of the present invention that is configured to provide health care for a person under test by preparing and recording every day the time series data including an oxidation/reduction potential value of a body of the person and the date and time at which the measurement is done and by acquiring a daily change in the living body including tendency of a menstrual cycle and an ovulation day, restoration after disease, etc., A perspective view and a block diagram of a health care apparatus according to the second embodiment are same as that of FIGS. 1 and 2 illustrating the first embodiment, respectively, except that in the block diagram of the second embodiment a timer for counting day and time is included in the controller 24 of the body section 3. Accordingly, the date and time at which the measurement is done is also stored in the memory 23, together with the oxidation/reduction potential of the body.

Figure 8:
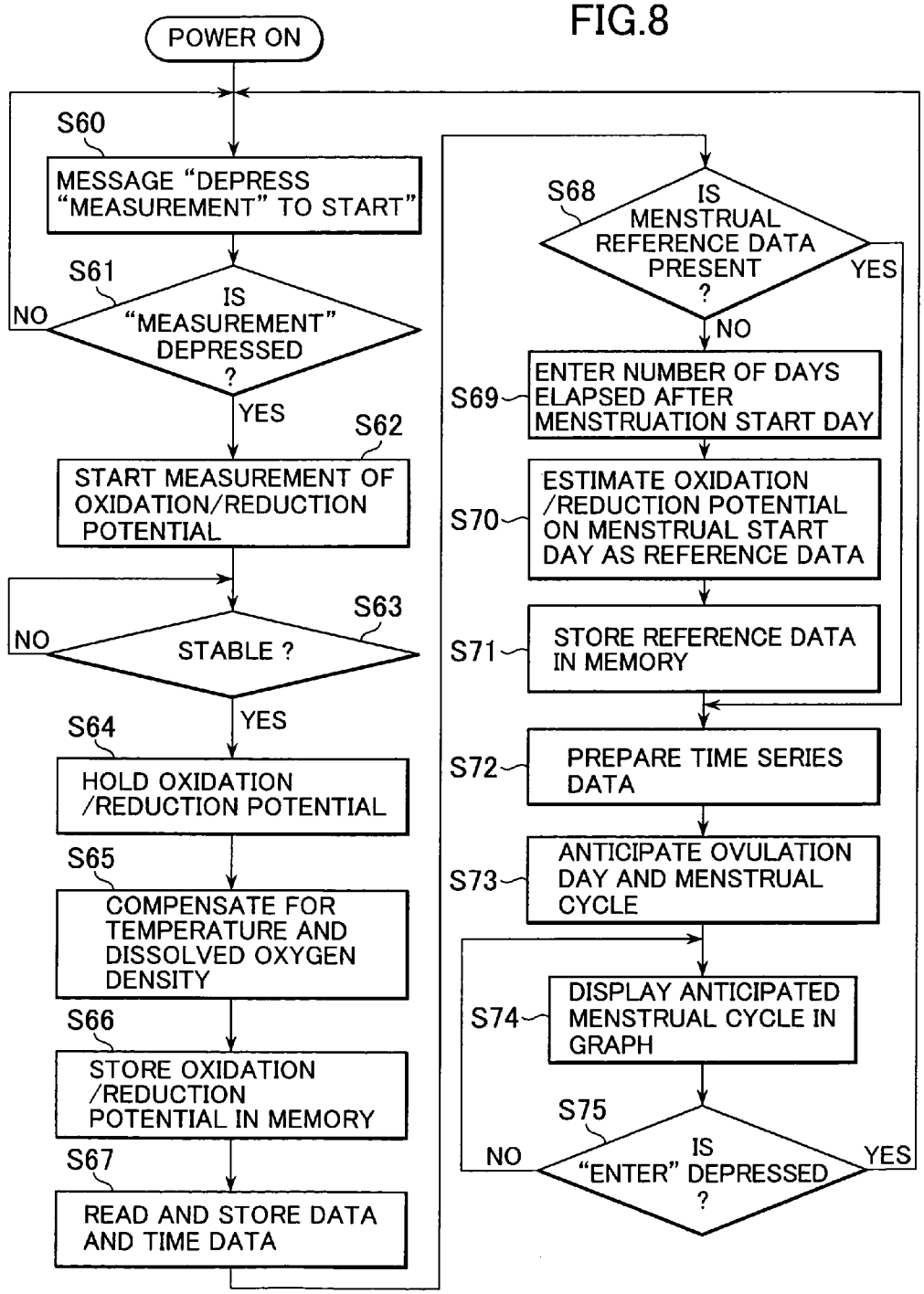
FIG. 8 is a flow chart illustrating a main routine for an operation of the health care apparatus according to a second embodiment of the present invention.
Figure 9:
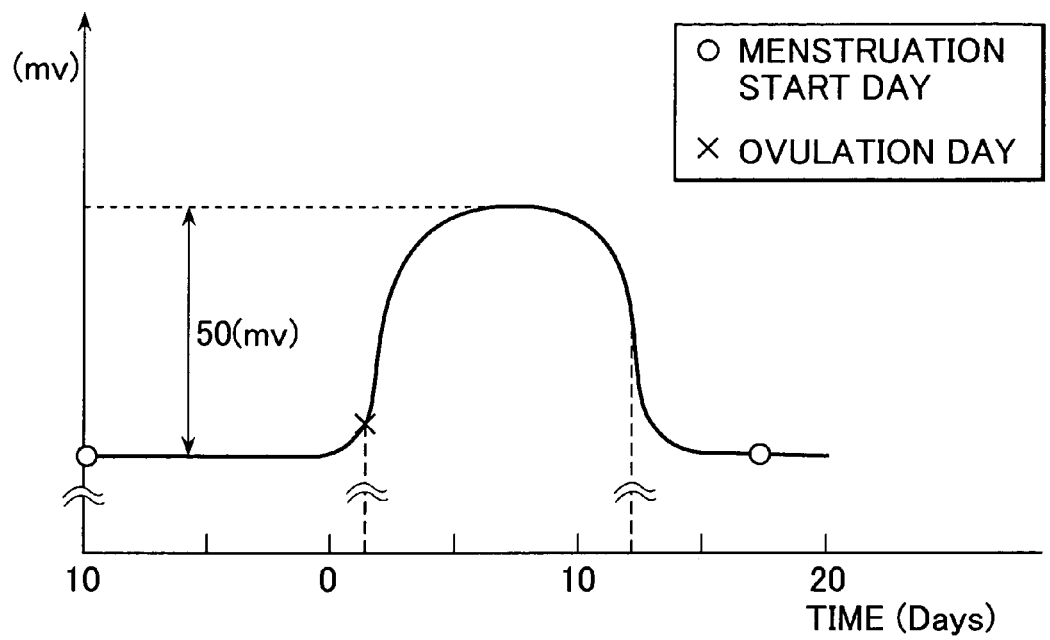
FIG. 9 is a graph illustrating an oxidation/reduction potential value along with a menstrual cycle.
Figure 10:
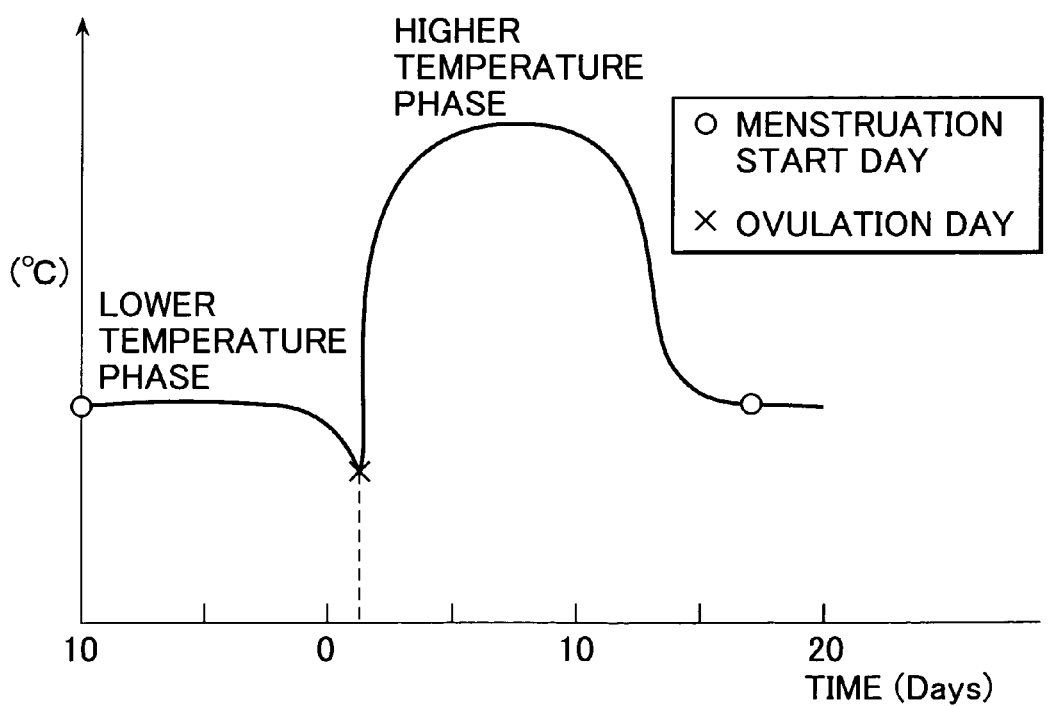
FIG. 10 is a graph illustrating a menstrual cycle according to a common basal body temperature method.

Operation of the health care apparatus of the second embodiment will be described in more detail with reference to FIGS. 8 to 10. In particular, FIG. 8 is a flow chart of health care procedure executed by acquiring tendency of a menstrual cycle and an ovulation day, by way of an example of a daily change in the living body. FIG. 9 is a graph illustrating an oxidation/reduction potential value along with a menstrual cycle. FIG. 10 is a graph illustrating a menstrual cycle according to a common basal body temperature method.

Initially, the power switch 9 in FIG. 1 is turned ON to power up the health care apparatus 1. Then, at step S60 in the flow chart of FIG. 8 a message is displayed on the display unit 8 for prompting to start measurement of an oxidation/reduction potential by depressing the measurement button on the operation panel 10. At step S61 a check is made to determine whether the measurement button is depressed or not. If not, the routine proceeds via "NO" branch to step S60 where the message remains displayed for prompting to depress the measurement button. But, if so, the routine proceeds via "YES" branch to step S62 where the measurement of oxidation/reduction potential is started.

Once the measurement of oxidation/reduction potential is started a check is made to determine whether the oxidation/reduction potential reaches stable condition or not at step S63. In this connection the oxidation/reduction potential is considered stable if any variation of the oxidation/reduction potential is maintained within the predetermined fixed allowable amplitude range for greater than the fixed time period. If not yet stable, the routine loops via "NO" branch to continue measurement. However, if stable, the routine proceeds via "YES" branch to step S64 where the oxidation/reduction potential is held at that stable condition to provide the stable oxidation/reduction potential value.

Then, in the same manner as the first embodiment, at step S65, the oxidation/reduction potential value is subjected to compensation for any error due to temperature and dissolved oxygen density to provide a temperature and oxygen density compensated oxidation/reduction potential value with higher precision. Then, at step S66, the temperature and oxygen density compensated oxidation/reduction potential value is stored in the memory 23. Furthermore, at step S67, the date and time data is retrieved from the timer in the controller 24 and it is stored in the memory 23, together with the oxidation/reduction potential value.

At step S68 a check is made to determine whether a menstrual reference data acting as the reference in preparing the time series data, i.e., the oxidation/reduction potential value at the menstruation start day is present in the memory 23 or not. If not, the routine proceeds to "NO" branch for preparing the necessary data. In particular, at step S69, the number of days elapsed after the menstruation start day and before the day at which the measurement of oxidation/reduction potential is made is entered. Thereafter, at step S70, the oxidation/reduction potential value at the menstruation start day is estimated with the aid of an ideal relation between the menstrual cycle and the oxidation/reduction potential value, which has been set in advance. Then, at step S71, the menstruation start day and the oxidation/reduction potential value at that day are stored in the memory 23 as the menstrual reference data.

However, if the menstrual reference data is present in the memory 23 at step S68, the routine bypasses steps S69 to S71 where the menstrual reference data is prepared, as described above, and directly proceeds to step S72 where the time series data is prepared based on the menstrual reference data and the oxidation/reduction potential values that have been measured up to now. Then, at step S73, the menstrual cycle and the ovulation day are anticipated on the basis of the time series data.

The relation between the menstrual cycle and the oxidation/reduction potential will be described with reference to FIGS. 9 and 10. In particular, FIG. 10 is a graph of the menstrual cycle resulting from the basal body temperature method, which is typically used as the base for estimating the menstrual cycle. Referring to FIG. 9, along with FIG. 10, the oxidation/reduction potential value during a lower temperature phase from the menstruation start day to the ovulation day is considered as the reference potential, then the oxidation/reduction potential value is rapidly increased in positive direction at the ovulation day, and thereafter, the oxidation/reduction potential value remains at increased level of approx. +50 (mV) relative to said reference potential during a higher temperature phase from the ovulation day to the next menstruation start day. Next, the oxidation/reduction potential is rapidly reduced in negative direction after elapsing the higher temperature phase, and approx. 2 to 4 days later, the oxidation/reduction potential returns to said reference potential. In this manner, the oxidation/reduction potential value has correlation with the basal body temperature, and therefore, it is possible to anticipate the menstrual cycle and the ovulation day.

At step S74 the result of anticipation of the menstrual cycle and the ovulation day is displayed on the display unit 8, together with the time series data that is displayed in graph, as shown in FIG. 9. Then, at step S75, a check is made to determine whether the enter button on the operation panel 10 is depressed or not. If not, the routine proceeds via "NO" branch to step S74 where the result of anticipation and the graph of time series data remain displayed, but if so, it proceeds via "YES" branch to step S60.

Furthermore, it is possible to know the degree of restoration during and after a disease and the effect of medicines or to know the effect of increase in bodily power due to an exercise as the time series change, if any daily change in the living body can be acquired.

It is apparent from the foregoing that a health care apparatus according to the present invention comprises: a measurement unit; an input unit; and a health index calculation unit, wherein said measurement unit measures an oxidation/reduction potential of a body of a person, said input unit enters at least one of living body information other than said oxidation/reduction potential of the body, and said health index calculation unit calculates a health index for judging a health condition, based on said oxidation/reduction potential of the body and said living body information. Accordingly, the health care apparatus can judge health condition of the person with higher precision by taking into account of the living body information for the person so that a normal person can clearly be distinguished from a person who suffers from a disease.

The health index calculation unit calculates the health index according to a health level that is determined by comparing said oxidation/reduction potential of the body and said living body information with an associated health level assessment criterion in which a plurality of health levels is set in advance. Accordingly, any suspected persons latently having any disease can easily be selected from among the normal persons, and the degree of progress of disease that the person suffers from can be indicated.

The health care apparatus further comprises: a difference calculation unit; a load effect calculation unit; and a load-to-health index calculation unit, wherein said difference calculation unit calculates any difference in oxidation/reduction potential before and after application of load to the body, said load including an action of doing an exercise, taking a meal, etc., said load effect calculation unit calculates any effect of load on the body by comparing said difference in oxidation/reduction potential before and after application of load with a load effect assessment criterion in which a plurality of load effect levels is set in advance, and said load-to-health index calculation unit calculates a load-to-health index for judging a health condition due to application of load to the body, based on said effect of load and said living body information. Accordingly, the person can know whether the load of doing an exercise or taking a meal is suitable for him or not.

The living body information may be blood pressure value. If the blood pressure increases due to presence of stress an oxidation of body fluid is produced due to active oxygen and lactic acid provided by the stress so that the oxidation/reduction potential of the body is increased. In other words, there is tendency of correlation between the blood pressure value and the oxidation/reduction potential value. Thus, it is possible to know the health condition of a person, taking into account of the presence of stress.

The living body information may be uric acid value. The oxidation/reduction potential is changed with the increase/decrease in uric acid which exhibits acidity. Therefore, there is tendency of correlation between the uric acid value and the oxidation/reduction potential value. Thus, it is possible to know the health condition of a person, taking into account of the morbidity and the degree of progress of disease such as gout, hyperlipemia, etc. of which condition is indicated by uric acid value.

The living body information may be blood sugar value or urine sugar value. If a person has insufficient insulin due to diabetes or excessive diet, for example, no sugar is dissolved so that the blood sugar value or urine sugar value becomes increased. As the result, fat is consumed as the energy source to form a ketone body that exhibits acidity within the body and to increase the oxidation/reduction potential value. Therefore, there is tendency of correlation between the blood sugar value or urine sugar value and the oxidation/reduction potential value. Thus, it is possible to know the health condition of a person, taking into account of the danger of diabetes or excessive diet that may lead to insufficient insulin.

The living body information may be the ratio of Na/K ions. This is provided by measuring both ion densities of sodium and potassium in the body fluid such as saliva, urine, sweat, blood, etc., using Polarograph type ingredient meter, for example. It is well known that excessive intake of "Na" is one of the factors for higher blood pressure and intake of "K" expels "Na" outside the body to lower the blood pressure. In other words, if "Na" ion density in extracellular fluid becomes higher the extracellular fluid is increased to keep the "Na" ion density constant. As the result, the blood pressure is increased to keep the flow rate of the blood. Because of correlation between blood pressure value and the oxidation/reduction potential value, as described above, it can also be said that there is tendency of correlation between the ratio of Na/K ions and the oxidation/reduction potential value. Thus, it is possible to know the health condition of a person, taking into account of blood pressure.

The living body information may be data of adiposity such as body weight, BMI or body fat, which has been utilized as the well known index for indicating the morbidity for adult noncommunicable diseases such as diabetes, hyperlipemia, etc. Such adult noncommunicable diseases may be indicated by blood pressure, uric acid value, or blood sugar value, which living body information has tendency of correlation with the oxidation/reduction potential value, as described above. Therefore, there is tendency of correlation between the data of adiposity and the oxidation/reduction potential value. Thus, it is possible to know the health condition of a person, taking into account of the morbidity for adult noncommunicable diseases.

The living body information may be pulse rate which has tendency of increase if heart and lung function becomes lower with the progress of adiposity. Therefore, there is tendency of correlation between the pulse rate and the data of adiposity such as body weight, BMI or body fat. Because of correlation between the data of adiposity such as body weight, BMI or body fat and the oxidation/reduction potential value, as described above, there is tendency of correlation between the pulse rate and the oxidation/reduction potential value. Thus, it is possible to know the health condition of a person, taking into account of the condition of heart and lung function.

Furthermore, the health care apparatus according to the present invention comprises: a measurement unit; a clock unit; a memory unit; and a living body change acquirement unit, wherein said measurement unit measures an oxidation/reduction potential of a body of a person, said clock unit determines date and time at which the measurement is done, said memory unit stores said oxidation/reduction potential of the body and said date and time as the time series data, and said living body change acquirement unit acquires any time series living body change such as a menstrual cycle, restoration after disease, etc., from said time series data. Accordingly, healthcare for a normal person or a person who suffers from a disease can easily be performed for longer period of time.

The health care apparatus further comprises a food indication unit, said food indication unit indicates at least one of the following food items: one is exhibiting the same oxidation/reduction potential as that of the person's body; and the other is exhibiting an oxidation/reduction potential desired for intake in view of the oxidation/reduction potential of the person's body, those food items being selected from among a food table listing several food items classified into a plurality of groups in advance according to the oxidation/reduction potential values that they inherently have. Accordingly, which food item having the same oxidation/reduction potential as that of body fluid of a person under test can be displayed, thereby enabling measurement with pleasure and spontaneously getting the knowledge about how much degree of oxidation/reduction the food items inherently has. On the other hand, by displaying food items each having oxidation/reduction potential desired for intake the person under test can know which food item is suitable for him and can control his body condition due to the food item.

The health care apparatus further comprises a dissolved oxygen density compensation unit, said compensation unit compensates for any effect of density of dissolved oxygen when measuring the oxidation/reduction potential of the body. Accordingly, the degree of oxidation/reduction of the living body can be displayed with higher precision.

The health care apparatus further comprises a temperature compensation unit, said compensation unit compensates for any effect of temperature of an object to be measured when measuring the oxidation/reduction potential of the body. Accordingly, the degree of oxidation/reduction of the living body can be displayed with higher precision.

What is claimed is:

1. A health care apparatus comprising:
a measurement unit;
an input unit; and
a health index calculation unit, wherein
said measurement unit measures an oxidation/reduction potential of a body of a person under test,
said input unit enters at least one of living body information other than said oxidation/reduction potential of the body, and
said health index calculation unit calculates a health index for judging a health condition, based on said oxidation/reduction potential of the body and said living body information;
said health care apparatus further comprising a health age judgment unit, wherein said health age judgment unit judges an age for health, based on said health index and according to a regression formula derived from correlation between said health index and the age.

2. A health care apparatus comprising:
a measurement unit;
an input unit; and
a health index calculation unit, wherein
said measurement unit measures an oxidation/reduction potential of a body of a person under test,
said input unit enters at least one of living body information other than said oxidation/reduction potential of the body, and
said health index calculation unit calculates a health index for judging a health condition, based on said oxidation/reduction potential of the body and said living body information;
said health care apparatus further comprising:
a difference calculation unit;
a load effect calculation unit; and
a load-to-health index calculation unit, wherein
said difference calculation unit calculates any difference in oxidation/reduction potential before and after application of load to the body, said load including an action of doing an exercise, taking a meal, etc.,
said load effect calculation unit calculates any effect of load on the body by comparing said difference in oxidation/reduction potential before and after application of load with a load effect assessment criterion in which a plurality of load effect levels is set in advance, and
said load-to-health index calculation unit calculates a load-to-health index for judging a health condition due to application of load to the body, based on said effect of load and said living body information.

3. A health care apparatus, comprising:
a measurement unit;
a clock unit;
a memory unit; and
a living body change acquirement unit, wherein
said measurement unit measures an oxidation/reduction potential of a body of a person under test,
said clock unit determines date and time at which the measurement is done, said memory unit stores said oxidation/reduction potential of the body and said date and time as the time series data, and said living body change acquirement unit acquires any time series living body change such as a menstrual cycle, restoration after disease, etc., from said time series data.

4. A health care apparatus comprising:

a measurement unit;

an input unit; and a health index calculation unit, wherein said measurement unit measures an oxidation/reduction potential of a body of a person under test, said input unit enters at least one of living body information other than said oxidation/reduction potential of the body, and said health index calculation unit calculates a health index for judging a health condition, based on said oxidation/reduction potential of the body and said living body information;

said health care apparatus further comprising a dissolved oxygen density compensation unit, wherein said compensation unit compensates for any effect of density of dissolved oxygen when measuring the oxidation/reduction potential of the body.

5. A health care apparatus comprising:

a measurement unit;

an input unit; and a health index calculation unit, wherein said measurement unit measures an oxidation/reduction potential of a body of a person under test, said input unit enters at least one of living body information other than said oxidation/reduction potential of the body, and said health index calculation unit calculates a health index for judging a health condition, based on said oxidation/reduction potential of the body and said living body information;

said health care apparatus further comprising a temperature compensation unit, wherein said compensation unit compensates for any effect of temperature of an object to be measured when measuring the oxidation/reduction potential of the body.

* * * * *